(12) United States Patent
Xu et al.

(10) Patent No.: US 8,871,984 B2
(45) Date of Patent: Oct. 28, 2014

(54) PREPARING METHOD FOR XANTHOPHYLL CRYSTALS WITH HIGHER CONTENT OF ZEAXANTHIN FROM PLANT OLEORESIN

(75) Inventors: Xinde Xu, Zhejiang (CN); Bin Shao, Zhejiang (CN); Hongjuan Chao, Zhejiang (CN); Xuejun Lao, Zhejiang (CN); Xiaoxia Sun, Zhejiang (CN)

(73) Assignee: Zhejiang Medicine Co., Ltd., Xinchang Pharmaceutical Factory, Shaoxing, Zhejiang (CN)

( * ) Notice: Subject to any disclaimer, the term of this patent is extended or adjusted under 35 U.S.C. 154(b) by 115 days.

(21) Appl. No.: 13/521,044

(22) PCT Filed: Mar. 18, 2010

(86) PCT No.: PCT/CN2010/071061
§ 371 (c)(1),
(2), (4) Date: Jul. 7, 2012

(87) PCT Pub. No.: WO2011/082560
PCT Pub. Date: Jul. 14, 2011

(65) Prior Publication Data
US 2012/0296126 A1    Nov. 22, 2012

(30) Foreign Application Priority Data
Jan. 7, 2010  (CN) .......................... 2010 1 0039569

(51) Int. Cl.
C07C 27/02 (2006.01)
C07C 29/09 (2006.01)
C07C 29/56 (2006.01)
C07C 403/24 (2006.01)
C09B 61/00 (2006.01)

(52) U.S. Cl.
CPC ........... *C07C 403/24* (2013.01); *C07C 2101/16* (2013.01); *C09B 61/00* (2013.01)
USPC .......................................... 568/816; 568/834

(58) Field of Classification Search
USPC ................................................. 568/816, 834
See application file for complete search history.

(56) References Cited

U.S. PATENT DOCUMENTS

| | | | |
|---|---|---|---|
| 7,271,298 B2 * | 9/2007 | Xu et al. ........................ | 568/816 |
| 7,485,738 B2 * | 2/2009 | Xu et al. ........................ | 554/125 |
| 2007/0265351 A1 * | 11/2007 | Kumar et al. .................. | 514/725 |

FOREIGN PATENT DOCUMENTS

CN    101124944 A  *  2/2008

OTHER PUBLICATIONS

He, W. et al. CN 101124944 A (English translation).*

* cited by examiner

*Primary Examiner* — Fereydoun G Sajjadi
*Assistant Examiner* — Medhanit Bahta
(74) *Attorney, Agent, or Firm* — Global IP Services; Tianhua Gu

(57) ABSTRACT

The invention makes public a method for preparing xanthophyll crystals with higher content of zeaxanthin from plant oleoresin. The current methods generally are to get quite pure crystal forms of xanthophyll or zeaxanthin, and they refer to several separation steps. The invention mixes the xanthophyll diester-containing plant oleoresins and food grade alcohol solvents to form smooth solution, and then soap-dissolve the solution under an alkaline environment; then replenish organic solvents and emulsifiers into the reaction solution and drop some alkali solution into the solution to make partial xanthophyll crystals be transformed to be zeaxanthin through epimerization reaction; after the reaction is finished, add the mixed solvents of alcohol solvent and water to separate out the crystals; use the method of centrifugation or filtration to get the crystals; wash the crystals several times with the mixed solution of deionized water and alcohols to remove the impurities among the crystals; recrystallize the gained crystals with absolute ethyl alcohol, and then dry the crystals to get the products. The invention can gain mixture of crystals that contain xanthophyll and zeaxanthin at one time in quite high collection rate.

10 Claims, No Drawings

PREPARING METHOD FOR XANTHOPHYLL CRYSTALS WITH HIGHER CONTENT OF ZEAXANTHIN FROM PLANT OLEORESIN

FIELD OF THE INVENTION

The present invention relates to the production of carotinoid, and in particular a method for production of xanthophyll crystals with higher content of zeaxanthin from plant oleoresin (especially, marigold oleoresin).

BACKGROUND OF THE INVENTION

Carotenoids are widespread in nature a kind of yellow to red substance. In different fruits and vegetables, there are different types of carotenoids, such as β-carotene in carrots, lutein in marigold flowers, zeaxanthin in strawberry, lycopene in tomato, capsanthin and capsochrome in chili class plants. In some dark fruit and vegetables, egg, fish, crustaceans, birds, algae and bacteria more carotenoids are existed, wherein the content of lutein is higher. In recent years, a number of animal and human trials showed that the beneficial effects of carotenoids. Carotenoids may be generally divided into the two sub-categories, namely, a relatively strong polarity of xanthophylls or oxygenated carotenoids, such as lutein, zeaxanthin, astaxanthin, and the non-polar of hydrocarbon carotenoids, such as β-carotene, lycopene. These two carotenoids of subclass, each contains at least nine conjugated double bonds, which not only gives the color features of carotenoid, also has strong antioxidant function in disease control, they can stop or prevent, like cancer, arteriosclerosis, cataracts, pigmentation and other degenerative diseases. And because carotenoids efficient scavenging of reactive oxygen free radicals and prevent free radicals generated, they can limit the damaging effects of oxidative free radicals.

For all carotinoid, due to their potential capability to prevent one kind of age related macular degenerations (ARMD), scientists and the public have paid more and more attention to the xanthophyll and zeaxanthin. Xanthophyll and zeaxanthin are the only two types of carotinoid existing within the spot area (macular degeneration) of human being's retina, and the area is closely related to the visual sensitivity of human beings (Bone et al. Invest. Ophthamal. Vis. Sci. 34:2033-2040, 1993). Usually eating of fruits and vegetables that are rich in xanthophyll and zeaxanthin can reduce the risk of getting aged macular degeneration by 43% (Seddon et al. J. Am. Med. Assoc. 272:1413-1420, 1994), and the metabolic pathway of xanthophyll and zeaxanthin for preventing aged macular degeneration has been cleared at present. The Food and Drug Administration also considers xanthophyll and zeaxanthin as (GARS), it means "generally recognized as safe". Therefore, these carotinoid can be used by themselves or together with other materials as nutritional supplements and food coloring agents, as well as can be used clinically for preventing aged macular degeneration and cancer, etc.

The constitutional formulas of xanthophyll and zeaxanthin are as follows respectively, they are isomers, the only difference between zeaxanthin and xanthophyll is the position of double bonds on one (not two) end ring, the position of the double bonds on the two end rings of the former is symmetrical, but that of the latter is asymmetrical, i.e. the straight chain part of the xanthophyll and zeaxanthin' each molecule is the conjugation structure having double bonds and single bond alternatively. In the molecule of zeaxanthin, the molecule conjugation structure extends to the first bond on the two end rings, but the degree of conjugation structure of xanthophyll is lower, because its double bonds on one of its end rings do not form a correct arrangement as a complete conjugation structure, and the difference of molecular structure results in xanthophyll and zeaxanthin have some differences in function properties.

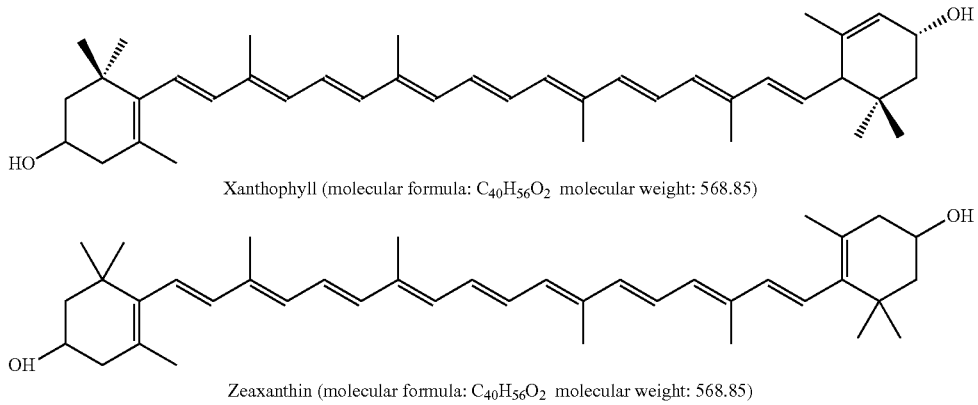

Xanthophyll (molecular formula: $C_{40}H_{56}O_2$ molecular weight: 568.85)

Zeaxanthin (molecular formula: $C_{40}H_{56}O_2$ molecular weight: 568.85)

As a kind of natural pigments, xanthophyll and zeaxanthin exist widely in nature, they mainly exist in higher plants, algae, fishes, shell class and bacterias, and they exist in the forms of ester in the body of living beings. Among these living beings, the marigold flower is a kind of good source for xanthophyll and zeaxanthin, it has about 2 g xanthophyll class materials in 100 g marigold fresh flowers, in which xanthophyll is more than 90%, and the rest are zeaxanthin and a few other carotinoid. It is the same as marigold flowers, in other kinds of higher plant and algae sources, the proportion of xanthophyll is more than zeaxanthin, but in corns the proportion of zeaxanthin is more than xanthophyll. Further, in the molecular structure stereoisomerism is presented in the xanthophyll and the zeaxanthin, different sources have different stereoisomerisms, for example, (3R,3'R,6'R)-xanthophyll and (3R,3'R)-zeaxanthin in plant resources, but xanthophyll is existed in forms of (3R,3'R,6'R)-, (3R,3'R,6'S)-, and (3R,3'S,6'S)- in animal resources, such as in fishes and shells.

Since the chemical synthesis lutein involves multi-step reaction, time-consuming, costly. Economical and easy method for large scale production of xanthophyll crystals is extracted, isolated and purified from natural sources. Many vegetables and fruits, such as spinaches, broccolis, cabbages and corns, etc, are quite rich in xanthophyll, but marigold flowers and calendulas are the richest sources of xanthophyll, of course, there also exists other carotinoid in these plants. The xanthophyll in plants usually exists in forms of single ester and double ester which usually is formed through esterification between the xanthophyll and some C12-C18 long-chain aliphatic acids.

Generally, we use organic solvents to extract xanthophyll ester from plants, preferentially from marigold flowers, calendulas and other dark green vegetables, and these organic solvents are quite easy to be separated. The marigold peaberry extract (marigold oleoresin) is a very good xanthophyll ester source, and the other classes of carotinoid are relatively not rich in it. After hydrolyzed under alkaline conditions, the xanthophyll crystals will be dissociated, wash off the fatty acid salt gotten from the soap-dissolving process, the xanthophyll crystals is further purified.

Meanwhile, as the above description, since the conjugated double bond in the molecular structure, which makes the zeaxanthin having stronger antioxidant activity than the xanthophyll, and the zeaxanthin takes a important effect for the health of human eyes. In fact, some researches in the middle to late 1980s had also proved that they mainly were zeaxanthin in the small area at the center of human eyes' macula lutea. They leave the concave concentrically and get close to the circum of the macula lutea, so the quantity of zeaxanthin gradually becomes less, and the quantiy of xanthophyll gradually becomes more. At the circum of the macula lutea, xanthophyll is the main xantheins.

This also can be found from the proportion change between xanthophyll and zeaxanthin in different parts of natural and human tissues, in the marigold flowers, the raw materials of xanthophyll, the proportion between xanthophyll and zeaxanthin is about 10-12:1, the proportion is about 3-5:1 in human blood, the proportion is 3:1 at the circum of retina macula lutea, but at the center of macula lutea the proportion is completely opposite, and it is 1:3. The recent researches have found that in an isomer of zeaxanthin at the central area if macula lutea, the internal compensation (3R,3'S,meso)-zeaxanthin took quite a lot proportion, and the proportion will be less, if it is closer to the periphery. More and more evidences have proved that the meso-zeaxanthin in macula lutea is gotten through lutein by epimerization transposition resulting, because it almost can not detect this kind of isomers of zeaxanthin in nature, human blood and other human tissues.

The distribution proportion change of xanthophyll and zeaxanthin in human eyes just proved the important and unique effects of zeaxanthin, in particular, the internal compensation zeaxanthin, for the health of human eyes. Actually, many human experiments also have proved that it will take a better effect for the complex use of xanthophyll and zeaxanthin, so most of the eye care products that contain xanthophyll on the market usually are added with certain quantity of extra zeaxanthin, i.e. it adds with xanthophyll and zeaxanthin respectively according to certain proportion in the application partition. However, the respective addition of xanthophyll and zeaxanthin must bring many unnecessary troubles for the purchase of raw materials, the operation of production process and product quality control. If it can be realized that some part of the xanthophyll forms zeaxanthin through epimerization during the process of making xanthophyll, thereby the result product can contain xanthophyll and zeaxanthin and keep the required proportion. Thus, it can just add one kind of carotinoid agents that contains certain proportion of xanthophyll and zeaxanthin, and this will result in much convenience for the subsequent product application process.

At present, there also are some patents and essays that refer to the method to prepare xanthophyll crystals in large scale from the peaberry of marigold or the method to gain zeaxanthin crystals through the epimerization transposition of xanthophyll. The targets of these essays generally are to get quite pure crystal forms of xanthophyll or zeaxanthin, and they refer to several separation steps.

U.S. Pat. No. 5,382,714 describes to separate and purify xanthophyll through washing the soap-dissolved marigold oleoresin under a quite low temperature and crystallizing the mixed solvent under a low temperature. The purification process not only is time-consuming, but also uses chlorinated organic solvents, so the products gained are not fit for being used in foods and medicines. The proportion between xanthophyll and zeaxanthin in the products do not change much compared with the raw materials.

U.S. Pat. No. 5,648,564 describes a method to separate xanthophyll crystals, it soap-dissolves xanthophyll diester-containing the propylene glycol solution of marigold oleoresins at first, and then it will recrystallize them. There are also several defects in this process: first, since the viscosity of propylene glycol is quite strong, it requires a quite high temperature during the soap-dissolving process or the following process, the entire system needs to be kept above 70° C. for about 10 hours, this obviously is disadvantageous for the stability of xanthophyll, the cis-trans isomers of xanthophyll also will change, what's more, the following separation processes, such as centrifugation and filtration, are also quite difficult; second, the collection rate of xanthophyll is quite low, it only is about 59%, and the xanthophyll content in the products is also not high.

U.S. Pat. No. 6,262,284 describes a method to use tetrahydrofuran to extract and soap-dissolve carotinoid from marigold dry flowers, it uses plenty of organic solvents during the process, these solvents are harmful to the stability of xanthophyll, and it may result in deterioration that is caused by overoxidation.

U.S. Pat. No. 6,329,557 describes a method to extract xanthophyll crystals from marigold oleoresins through large industrial scale. The defect of the process is to use plenty of organic solvents, such as normal hexanes, ketones, etc, and these solvents are not fit for using in foods.

U.S. Pat. No. 6,380,442 reports a method to separate carotinoid from plants, the method is also not attractive for industrial production, because it will use a lot of water (at least 30 times the raw materials) during the production process, and the operation is quite difficult.

U.S. Pat. No. 6,743,953 describes to use organic solvents to separate and purify xanthophyll from marigold oleoresins. It uses several organic solvents, such as ipa, ethyl acetate, normal hexane, acetone and methanol, etc, during the process, the operation is miscellaneous, the organic solvent consumption is quite large, and the collection rate is low. Therefore, this method is also not fit for industrial production.

In U.S. Pat. No. 7,271,298, it makes public a method that uses absolute ethyl alcohol as the solvent to get higher content xanthophyll crystals in high collection rate through simple technology, and this method also do not consider to enhance the proportion of zeaxanthin for the gained crystals.

U.S. Pat. No. 5,780,693 designs a routine to produce zeaxanthin taking xanthophyll as the raw materials. In general, it mainly uses dimethyl sulfoxide or the mixture of dimethyl sulfoxide and saturated alkane and/or arene organic solvents as the solvents and uses alkali hydroxides as catalysts to produce zeaxanthin through transposition of xanthophyll. Furthermore, it uses the organic solvents, such as normal hexanes, normal heptanes, dichloromethane, methyl alcohols, etc, during the reaction process. It is obviously improper to use these toxic solvents to produce food grade or medicine grade zeaxanthin.

U.S. Pat. No. 7,485,738 describes to use xanthophyll as the raw materials to gain high purity internal compensation zeaxanthin through epimerization with the catalysis of strong organic alkali, and the gained zeaxanthin crystals through this technology do not contain or contain very few xanthophyll.

The described methods in the above patents have several defects as follows: 1) using some toxic organic solvents during the processes, it is quite difficult or impossible to remove these solvents completely, and this results in that the produced xanthophyll or zeaxanthin crystals are unfit for being used as edible products of human beings; 2) or the used organic solvents are quite high in viscosity, the operation during the process of separation and purification is quite difficult, in order to gain higher content crystals, it needs a treatment process with several steps, so it is not suitable for industrial production; 3) or the collection rate of carotinoid is quite low, since it refers to several steps during the process, it results in the low product collection rate, and it is only about 50%. In particular, when using marigold flowers as the raw materials to gain the mixtures of zeaxanthin and xanthophyll through isomerization reaction to transform xanthophyll crystals partially after it gained xanthophyll crystals through soap-dissolving reaction, separation and retification, the collection rate is lower. 4) or the single concentration of xanthophyll or zeaxanthin in the products is quite high, they can not reach the purpose to adjust xanthophyll and zeaxanthin concentration through controlling the reaction process according to the requirements.

Therefore, it is necessary to find a method that is suitable to produce high purity xanthophyll and zeaxanthin in industrial scale, which uses as few as possible toxic organic solvents, refers to as few as possible steps, owns quite high collection rate, and can control the reaction parameters according to the needs, so that it can reach the purpose to adjust the xanthophyll and zeaxanthin concentration in the products.

SUMMARY OF THE INVENTION

In order to overcome the defects of the above described methods, the invention provides a preparing method for xanthophyll crystals with higher content of zeaxanthin from plant oleoresin, and it can achieve the purpose to be convenient and to adjust the zeaxanthin content in xanthophyll crystals effectively.

Therefore, the invention adopts the following steps:

a) mix the xanthophyll diester-containing plant oleoresin and food grade alcohol solvents through stirring to form uniform free-pouring mixed liquor. Next, soap-dissolve this mixed liquor 3-5 hours under an alkaline environment, i.e. with a temperature between 40° C. and 85° C.

b) replenish the mixed liquor gotten from step a) with organic solvents and emulsifier and stir it to be well-distributed;

c) drip strong alkaline solution into the mixed liquor gotten from the step b) to result in the epimerization of partial gained xanthophyll crystals to transform them to be Zeaxanthin, and then adjust the reaction time and temperature in accordance with the required proportion between the xanthophyll and zeaxanthin;

d) use the mixed solvents consisting of deionized water and alcohols solvents to dilute the reaction solution gotten from step c), to make the solute in the solution be lowered to 10-50% in volume concentration, the dosage of deionized water and alcohols solvents is 2-10 times and 0.5-2 times in weight of raw material plant oleoresin respectively, and then heat up the diluted reaction solution to 60-75° C. and stir 0.5-2.0 hours slowly to make carotinoid be separated out in a form of granular crystals;

e) use the method of centrifugation or filtration to get the crystals formed in step d);

f) use 60-85° C. hot water to rinse the crystals gotten from step c) 2-3 times until the mother liquor is close to be colorless;

g) In order to make the final product to be dried easy, before desiccation use absolute ethyl alcohol to drip-wash the filter cake one time, and then use vacuum drying or freeze drying to get xanthophyll crystals, which results final loss on drying to be less than 5%.

The used plant oleoresins in the invention are extracts of marigold flowers, calendulas, spinachs, strawberries, broccolis, corns, cabbages, in these raw materials, the xanthophyll content in marigold flower extracts is relatively quite high, and they are the preferential raw materials. Due to the difference of varieties, planting conditions, harvest periods and extract methods, these oleoresins contain 5-30% xanthophyll diesters and a few other carotinoid, such as all-trans zeaxanthin, α- and β-cryptoxanthin and β-carotenes, etc.

According to ultraviolet visible ray spectrophotometry analysis and HPLC analysis, the final product contains 75-95% carotinoid, which contains 15%-95% all-trans xanthophyll, 85%-5% zeaxanthin, 0.1-1.0% other possible geometric isomers, as well as less than 1.0% other carotinoid. This microscale of other carotenoid is safe for human, because they are also contained in food sources, the other carotenoid is also existed in human blood serum with a concentration being higher than xanthophyll in the blood serum.

In the produced final crystallization products through this technology, there are no residuals of toxic organic solvents and other toxic compounds, so it is suitable to be used for human.

In step a) of the invention, usually dissolve the plant oleoresins in the food grade alcohol solvents that is 0.5-2.0 times that of the plant oleoresins in volume, and through stirring, xanthophyll esters and other kinds of impurities, such as waxes, resins, other carotinoid and pigments, etc, are dissolved or dispersed in these solvents to form a kind of well distributed solution; Add aqueous alkali solutions (such as NaOH, KOH, sodium methoxide or sodium ethoxide) into the well distributed solution to carry out soap-dissolving, the needed quantity of alkali is 0.5-6.0 times the weight of xanthophyll diester-containing oleoresins, xanthophyll, zeaxanthin and other carotinoid are dissociated out of the solution during this process, at the same time, the fatty acid in plant oleoresins (such as myristic acid, palmitic acid, stearic acid, etc) react with sodium or potassium to form soda soap or potash soap, the used food grade alcohol solvents are carbinols, ethyl alcohols, isopropyl alcohols, propyl alcohol, etc, and ethyl alcohols are a preferential option.

In the step b) and c) of the invention, replenish a certain quantity of organic solvents to enhance the solubility of the dissociated carotinoid in this solution, the dosage of organic solvents are 1.0-3.0 times the volume of the same plant oleoresin weight, the organic solvents can be alcohols solvents, such as ethanol, isopropyl alcohol, propanol, propylene glycol, etc, they also can be esters solvents, such as ethyl acetate, ethyl ester isobutyl paraben, etc, and they also can be other organic solvents, such as dimethyl sulfoxide, methylene chloride, etc. It can make carotinoid be dissolved better to add a certain quantity of emulsifiers, the used emulsifiers can be Tween emulsifiers, such as Tween-60, etc, they also can be Span emulsifiers, such as Span-40, etc, the dosage of emulsifiers is 0.4-1.0 times the weight of xanthophyll crystals in plant oleoresins, in this way, after it is replenished certain quantity of strong alkalis (the dosage of strong alkalis is 0.1-1.0 times the weight of xanthophyll diester-containing plant oleoresins) by dropping, it does not need extra steps to separate out the xanthophyll crystals, and it can directly make partial xanthophyll be transformed to zeaxanthin by epimerization. The proportion between the xanthophyll and zeaxanthin in the reaction products can be monitored through using high performance liquid chromatography on the samples. In accordance with the required proportion between the xanthophyll and the zeaxanthin, it can adjust the reaction time and temperature, the selection scope of reaction time is 0.5-6.0 hours, and the selection scope of temperature is 60-90° C.

In step e) of this invention, separates out the formed crystals in step d) by traditional separation process, such as centrifugation, filtration and pressure filtration, etc. Before separating the crystals, in order to further reduce the concentration of crystals to make the following separation operation process to be carried out easy, proper quantity of hot water is used to dilute the solution. After the separation operation, the impurities, such as fatty acids, salts, soaps, water-solubility chlorophylls and flavones, are transferred into the mother liquor, and the crystals, such as xanthophyll and zeaxanthin, are left in the filter cake.

What need to be explained is that the purity of the final products, the proportion between xanthophyll and zeaxanthin, the collection rate of carotenoid crystals not only depends on the addition of the solvents during the soap-dissolving process and the addition of the alcohol solvents during the dilution process, as well as the addition, reaction time and reaction temperature of alkalines during the isomer reaction process, but also depends on the crystallization time before washing.

If the proportion of solvents is too low during the soap-dissolving process, it will make the viscosity of the solvents be quite strong, and this is not good for the following separation operation; if the proportion of the solvents is too high, it will make the concentration of xanthophyll in the solution become low, and this is not good for complete soap-dissolving, which will lower the collection rate of the products and the content of crystals. This is why partial organic solvents need to be replenished before isomerization reaction, because the solubility of oleoresins is relatively quite large, and what gained after soap-dissolving reaction are carotenoid crystals, the solubility of these crystals in organic solvents will be lowered a lot, but it must make them be dissolved and take part in reaction in order to make it be transformed to be zeaxanthin, so it is necessary to replenish certain quantity of organic solvents after the soap-dissolving reaction is finished and before the isomerization reaction is started. On the one hand, it will not dilute the concentration of oleoresins before soap-dissolving reaction, but it can make the carotenoid oleoresins to finish soap-dissolving within a quite short period to enhance the carotenoid content in the final products. On the other hand, it can also ensure the sufficient dissolution of the reactants, i.e. the dissociative carotenoid crystals, so that it can make the isomerization reaction be controllable.

It is also very important to add alkalis in turn at different reaction stages. Before the dissociative carotenoid crystals gotten from soap-dissolving plant oleoresins have not be dissolved in the organic solvents to carry out isomerization reaction, the concentration of alkalis can not be too high, otherwise partial carotenoid oleoresins and generated carotenoid crystals will be lost by the oxidization of high concentration alkali, in a serious situation they even will be carbonized. For avoiding this situation it is necessary to add different quantity of alkalis in different stages. The purpose to dropping add strong alkalis during the later process of transforming xanthophyll into zeaxanthin by isomerization is the same reason.

Before the isomerization reaction, it is good to add certain quantities of emulsifiers for promoting isomerization reaction. Since adding certain quantities of aqueous alkalis as the catalyst of the reaction during the process of soap-dissolving and isomerization reaction will bring in a little water inevitably, and the water will lower the solubility of the carotenoid crystals in organic solvents greatly to result in reducing the rate of isomerization reactions. Using certain quantities of emulsifiers can reduce the bed influence by the adding water for the carotenoid crystals. Also, it can enhance the solubility of carotenoid. Furthermore, a few of emulsifiers can increase the contact opportunity between the catalysts and carotenoid crystals, and it will make the isomerization reaction be easier to be carried out.

In addition, the rectification process of alcohol solution before separating the final carotenoid crystals will also influence the content and collection rate of the products. It will lower the collection rate of the products to add in too many alcohols during the dilution process, and it will increase the operation difficulty to add too less alcohols. The time to precipitate crystals also can not be too short, otherwise, it will lower the collection rate.

The advantages of the invention are as follows: 1) using plant oleoresins as the raw materials to get the crystals that contain xanthophyll and zeaxanthin at one time through two continuous reactions, i.e. the soap-dissolving reaction and isomerization reaction, the proportion between xanthophyll and zeaxanthin in the crystals can be adjusted through controlling reaction conditions in accordance with the requirements, it is convenient for the following product application, and it can effectively avoid the inconvenience in purchasing, storage and operation, because it needs to mix the xanthophyll and the zeaxanthin respectively while applying the products. 2) The method can gain mixture of crystals of xanthophyll and zeaxanthin with quite high collection rate through a series of condition optimizing, the process does not need extra operation to purify the xanthophyll crystals, and the process can carry out isomerization reaction directly. The method of present invention has much higher collection rate compared with the current technology, Also the method can get higher purity xanthophyll crystals and get the mixture of crystals of xanthophyll and zeaxanthin by the isomerization of partial xanthophyll crystals; 3) Adding the organic solvents and base catalysts in turn, it not only can protect the normal process of the reaction, but also can shorten the reaction time as much as possible and ensure the complete reaction, and can avoid the destruction effect of the strong alkalis to the reaction products. 4) During the starting stage of the isomerization reactions, increase the solubility of carotenoid crystals in the organic solvents, and effectively increase the contact opportunities between the base catalysts and the reaction substrates to make the reaction be more complete. 5) Since the used solvents during the process are water and low grade alcohols or esters, their viscosity is quite low, the separation operation process is easy, and no extra organic solvent is used for the recrystallization rectification process. Therefore, the method of the present invention is very economic and is suitable for large scale industrial production.

For well understanding the present invention, a detailed introduction of preferred embodiments is as follows.

DETAIL DESCRIPTION OF THE INVENTION

Implementation Example 1

Mix 1000 g marigold oleoresins (total xanthophyll content is 15.2% in weight) and 2000 mL isopropyl alcohol, heat them to 40° C., stir them until becoming a kind of well distributed flowing solvent, drip 405 mL 45% NaOH solution into them slowly while stirring them, the dripping time is 60 minutes, and let it carry out soap-dissolving 5 hours under this temperature.

Heat the reaction solution to 60° C., add isopropyl alcohol solution 2400 mL, emulsifier Tween-80 80 g, and then stir the reaction solution 0.5 hour to make it be mixed evenly. Drip 37% $CH_3ONa$ solution 240 mL slowly, the dripping time is 1.0 hour, heat it to 70° C. at the same time, and stir it to make it react for 0.5 hour.

Add 2000 mL deionized water and 200 mL ethyl alcohol after the reaction is completed, keep the temperature of the solution at 60° C. during the dilution process, and stir it slowly for 30 minutes. Separate the gained crystals by centrifugation, the process is quite easy, and it can be finished within 10 minutes. Wash the collected crystals 2-3 times with 60° C. hot water until the eluate is almost colourless, wash the crystals with dripping absolute ethyl alcohol at last, and then dry it in vacuum under 40° C. until its loss on drying is less than 5%.

At last, we can get 144.6 g finished products, 87.2% of them is carotinoid (it can be analyzed through ultraviolet visible rays luminosity instruments), the carotnoid contains 95.1% all-trans xanthophyll, 4.8% all-trans zeaxanthin (it can be analyzed through HPLC), and the rest are other microscale carotinoid. The collection rate of total carotinoid is 82.95%.

The finished product does not contain toxic organic solvents, and it is suitable to be used in the form of nutritional supplements and food additives. The application form of this crystal can be oil suspension (it is emulsified through mixing with plant oil), peaberry (it is the microcapsule gained through atomizing condensation), dry powder (it is the microcapsule gained through atomizing drying), etc.

Implementation Example 2

Mix 500 g marigold oleoresins (total xanthophyll content is 14.5%) and 250 mL propyl alcohol, heat them to 85° C., stir them until they become a kind of even flowing solvent, drop 405 mL 45% NaOH solution into them slowly while stirring them, the dropping time is 60 minutes, and let it carry out soap-dissolving 3 hours under this temperature.

Cool the reaction solution to 60° C., add ethyl acetate solution 1500 mL, emulsifier Span-40 65 g, and then stir it 0.5 hour to make it be mixed evenly. Drop 50% sodium ethoxide solution 100 mL slowly, the dropping time is 1.0 hour, heat it to 80° C. at the same time, and stir it to make it react for 6.0 hour.

Add 1000 mL deionized water and 250 mL ethyl alcohol after the reaction is finished, keep the temperature of the solution at 60° C. during the dilution process, and stir it slowly for 120 minutes. Separate the gained crystals through filtration, the process is quite easy, and it can be finished within 30 minutes. Wash the collected crystals 2-3 times with 85° C. hot water until the eluate is almost colourless, wash the crystals with dropping absolute ethyl alcohol at last, and then dry it in vacuum under 40° C. until its loss on drying is less than 5%.

At last, we can get 61.0 g finished products, 85.6% of them are total carotinoid (it can be analyzed through ultraviolet visible rays luminosity instruments), it contains 15.2% all-trans xanthophyll in these carotinoid, 84.8% all-trans zeaxanthin (it can be analyzed through HPLC), and the rest are other microscale carotinoid. The collection rate of total carotinoid is 72.02%.

It does not contain toxic organic solvents in the products, and it is suitable to be used in the forms of nutritional supplements and food additives. The application form of this crystal can be oil suspension (it is emulsified through mixing with plant oil), peaberry (it is the microcapsule gained through atomizing condensation), dry powder (it is the microcapsule gained through atomizing drying), etc.

Implementation Example 3

Mix 1000 g marigold oleoresins (total xanthophyll content is 14.5%) and 2500 mL ethyl alcohol, heat them to 75° C., stir them until they become a kind of well distributed flowing solvent, drip 380 mL 50% NaOH solution into them slowly while stirring them, the dripping time is 60 minutes, and let them carry out soap-dissolving 4 hours under this temperature.

Cold the reaction solution to 60° C., add propyl alcohol solution 1200 mL, emulsifier Tween-60 60 g, and then stir it 0.5 hour to make them being mixed well distributed. Drip 37% sodium methoxide solution 100 mL slowly, the dropping time is 1.0 hour, heat them to 80° C. at the same time, and stir them to make them to react for 3.0 hour.

Add 1000 mL deionized water and 250 mL ethyl alcohol after the reaction is finished, keep the temperature of the solution at 60° C. during the dilution process, and stir it slowly for 120 minutes. Separate the gained crystals through pressure filtration, the process is quite easy, and it can be finished within 30 minutes. Wash the collected crystals 2-3 times with 85° C. hot water until the eluate is almost colourless, wash the crystals with dripping absolute ethyl alcohol at last, and then dry it in vacuum under 40° C. until its loss on drying is less than 5%.

At last, we can get 141.6 g finished products, 84.7% of them are carotinoid (it can be analyzed through ultraviolet visible rays luminosity instruments), the carotinoid contains 87.1% all-trans xanthophyll, 12.8% all-trans zeaxanthin (it can be analyzed through HPLC), and the rest are other microscale carotinoid. The total collection rate of xanthophyll is 82.71%.

Implementation Example 4-7

| Items | Steps | | | |
|---|---|---|---|---|
| | Implementation example 4 | Implementation example 5 | Implementation example 6 | Implementation example 7 |
| The numbers of the raw materials (g) and the xanthophyll content among them | 300 g/14.5% | 1500 g/13.6% | 480 g/15.4% | 600 g/14.6% |
| The types and quantities of solvents while carrying out soap-dissolving reaction | methyl alcohol/ 600 ml | ethyl alcohol/ 1200 ml | normal propyl alcohol/ 500 ml | ethyl alcohol/ 800 ml |

-continued

| Items | Implementation example 4 | Implementation example 5 | Implementation example 6 | Implementation example 7 |
|---|---|---|---|---|
| The types and quantities of base catalysts while carrying out soap-dissolving reaction | 37% sodium methylate solution/ 118 ml | 50% sodium ethoxide solution/ 816 ml | 50% KOH ethyl alcohol solution/ 1780 ml | 45% NaOH solution/ 400 ml |
| The types and quantities of replenishing solvents before the isomerization reaction | ethyl acetate/ 300 ml | ethyl alcohol/ 1500 ml | isopropyl alcohol/ 1200 ml | isobutyl acetate/ 1800 ml |
| The types and quantities of replenishing emulsifiers before the isomerization reaction | Tween-60/ 17.5 g | Span-40/ 204 g | Tween-80/ 52.0 g | Span-20/ 88.0 g |
| The types and quantities of dropping alkali liquor before the isomerization reaction | 50% sodium ethoxide solution/ 87 ml | 50% KOH ethyl alcohol solution/ 820 ml | 45% NaOH solution/ 330 ml | 37% sodium methylate solution/ 50 ml |
| The temperature of isomerization reaction | 90° C. | 60° C. | 70° C. | 85° C. |
| The time of isomerization reaction | 3.0 hours | 1.0 hours | 4.5 hours | 6.0 hours |
| The number of the final products (g) | 42.9 g | 178.8 g | 71.5 g | 72.5 g |
| The total carotinoid content (%, UV) in the final products | 76.4% | 82.3% | 74.8% | 88.4% |
| The proportion between xanthophyll and zeaxanthin in the final products (HPLC) | 94.6%/5.2% | 85.2%/14.5% | 30.4%/69.4% | 15.2%/84.7% |

Compare the Preferred Embodiments

Soap-dissolve 1000 g marigold oleoresins (the total xanthophyll content is 14.5%) in accordance with the technology described in U.S. Pat. No. 7,271,298 and gain carotinoid crystals 129.6 g after removing the impurities by alcohol solution, the content of carotinoid crystals is 93.2%, the product collection rate is 83.3%, and the carotinoid crystals contain 93.1% all-trans xanthophyll and 6.8% all-trans zeaxanthin.

Take the above described xanthophyll crystals 120 g to carry out epimerization reaction in accordance with the published method of U.S. Pat. No. 7,485,738, monitor the process of the reaction through HPLC chromatography, stop the reaction after 1.5 hours, remove the related impurities through alcohol solution again, finally we can get carotinoid crystals 71.3 g, the content is 85.6%, the proportion of all-trans xanthophyll is 88.1%, the proportion of all-trans zeaxanthin is 11.8%, and the collection rate of epimerization reaction is 54.6%.

The total collection rate of the above two steps of reactions is only 45.5%, and it is much lower than the product collection rate of the invention.

What is claimed is:

1. A method for preparing xanthophyll crystals containing a high content of zeaxanthin from plant oleoresin comprising the following steps:
    a) mix a xanthophyll diester-containing plant oleoresin and food grade alcohol solvents through stirring to form a uniform mixed liquor, add an alkali solution to soap-dissolve the mixed liquor for 3-5 hours at a temperature range between 40° C. and 85° C.;
    b) add organic solvent and emulsifier to the mixed liquor obtained from step a) and stir the mixture of the mixed liquor, organic solvent and emulsifier to form a well distributed mixed liquor;
    c) add drop-wise an alkali solution into the mixed liquor obtained from step b) to result in the epimerization of partially gained xanthophyll crystals to transform them to zeaxanthin;
    d) add deionized water and alcohol solvents to dilute the reaction solution obtained from step c) to lower the concentration of the solute in the solution to a range of 10-50%, heat the mixture to a temperature range of 60-75° C. and stir the mixture for 0.5-2.0 hours to separate out carotenoid granular crystals,
    wherein the dosage of deionized water and alcohol solvents are 2-10 times and 0.5-2 times the weight of the raw material plant oleoresin, respectively;
    e) subject said granular crystals to centrifugation or filtration;
    f) use water heated to a temperature range of 60-85° C. to rinse the crystals obtained from step e) 2-3 times;
    g) use absolute ethanol to wash the crystals obtained from step f) and vacuum dry or freeze dry the crystals to obtain xanthophyll crystals containing a high content of zeaxanthin with less than 5% moisture content.

2. The method of claim 1, wherein the plant oleoresin is extracted from marigold flowers, calendulas, spinaches, strawberries, broccolis, cabbages or corns.

3. The method of claim 1, wherein the amount of food grade alcohol solvents in step a) is 0.5-2.0 times the weight of the plant oleoresins.

4. The method of claim 3, wherein the alkali solution in steps a) and c) is NaOH, KOH, sodium methoxide or sodium ethoxide and wherein the amount of the alkali in step a) is 0.5-6.0 times the weight of the xanthophyll diester containing plant oleoresins for complete soap-dissolution and wherein the amount of the alkali in step c) is 0.5-1.0 times the weight of the xanthophyll diester containing plant oleoresins.

5. The method of claim 1, wherein the organic solvent is selected from the group consisting of alcohol solvents and esters and wherein the amount of the organic solvent is 1.0-3.0 times the weight of the plant oleoresins.

6. The method of claim 5, wherein the organic solvent is selected from the group consisting of ethanol, isopropyl alcohol, propanol, ethyl acetate and isobutyl acetate.

7. The method of claim 1, wherein in step c) the reaction time is 0.5-6.0 hours and the temperature range is 60-90° C.

8. The method of claim 1, wherein the alcohol solvents in steps a) and d) are methanol, ethanol, isopropyl alcohol or propanol.

9. The method of claim 2, wherein the amount of food grade alcohol solvents in step a) is 0.5-2.0 times the weight of the plant oleoresins.

10. The method of claim 9, wherein the alkali solution in steps a) and c) is NaOH, KOH, sodium methoxide or sodium ethoxide and wherein the amount of the alkali in step a) is 0.5-6.0 times the weight of the xanthophyll diester containing plant oleoresins for complete soap-dissolution and wherein the amount of the alkali in step c) is 0.5-1.0 times the weight of the xanthophyll diester containing plant oleoresins.

* * * * *